United States Patent
Gumbrecht et al.

(10) Patent No.: US 9,347,097 B2
(45) Date of Patent: May 24, 2016

(54) ARRANGEMENT FOR DETERMINING THE CONCENTRATION OF NUCLEIC ACIDS

(71) Applicant: Boehringer Ingelheim Vetmedica GmbH, Ingelheim am Rhein (DE)

(72) Inventors: Walter Gumbrecht, Herzogenaurach (DE); Jörn Mosner, Erlangen (DE); Sebastian Schmidt, Weisendorf (DE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 0 days.

(21) Appl. No.: 14/220,736

(22) Filed: Mar. 20, 2014

(65) Prior Publication Data

US 2014/0206578 A1 Jul. 24, 2014

Related U.S. Application Data

(62) Division of application No. 11/808,835, filed on Jun. 13, 2007, now Pat. No. 8,715,924.

(30) Foreign Application Priority Data

Jun. 14, 2006 (DE) .......................... 10 2006 027675

(51) Int. Cl.
- *C12M 1/00* (2006.01)
- *C12M 1/34* (2006.01)

(Continued)

(52) U.S. Cl.
CPC ............... *C12Q 1/686* (2013.01); *B01L 3/5027* (2013.01); *C12Q 1/6851* (2013.01); *B01L 7/52* (2013.01);

(Continued)

(58) Field of Classification Search
CPC ......... C12P 19/34; C12Q 1/68; B01L 3/5027; B01L 7/52
USPC .................. 435/6.1, 91.1, 91.2, 283.1, 287.2, 435/288.5, 288.7; 204/403.1; 422/68.1, 422/82.01, 174; 506/16; 536/23.1, 24.3

See application file for complete search history.

(56) References Cited

U.S. PATENT DOCUMENTS

| | | | |
|---|---|---|---|
| 4,683,195 A | 7/1987 | Mullis et al. | |
| 5,219,727 A | 6/1993 | Wang et al. | |

(Continued)

FOREIGN PATENT DOCUMENTS

| | | |
|---|---|---|
| DE | 101 26 341 A1 | 12/2002 |
| WO | WO-0194634 A2 | 12/2001 |

(Continued)

OTHER PUBLICATIONS

Chinese Office Action dated May 3, 2012, issued in corresponding Chinese Application No. 200710110070.2, with English translation.

(Continued)

*Primary Examiner* — Narayan Bhat
(74) *Attorney, Agent, or Firm* — Roberts Mlotkowski Safran & Cole, P.C.; David S. Safran

(57) ABSTRACT

An arrangement for determining the concentration of nucleic acids in a sample in a microfluidic device. In at least one embodiment, the arrangement having a) a first chamber into which a the sample is introduced, b) an element in the first chamber for carrying out a number of cycles of an amplification reaction to be carried out in cycles for amplifying nucleic acids, c) a second chamber, connectable to the first chamber by way of fluidic communication, equipped with an element to determine concentrations of amplified nucleic acids, d) a control unit to introduce a defined volume of a solution containing reagents for the amplification reaction into the first chamber and to transfer a defined volume from said first chamber to the second chamber.

10 Claims, 1 Drawing Sheet

(51) Int. Cl.
*C12M 3/00* (2006.01)
*C12Q 1/68* (2006.01)
*C12P 19/34* (2006.01)
*C12N 9/00* (2006.01)
*G01N 27/00* (2006.01)
*C40B 40/06* (2006.01)
*C07H 21/02* (2006.01)
*B01L 3/00* (2006.01)
*B01L 7/00* (2006.01)

(52) U.S. Cl.
CPC ........ *B01L 2200/143* (2013.01); *B01L 2200/16* (2013.01); *B01L 2300/0645* (2013.01); *B01L 2300/0816* (2013.01); *B01L 2300/0867* (2013.01); *B01L 2300/1822* (2013.01); *B01L 2400/0487* (2013.01); *B01L 2400/0633* (2013.01)

(56) References Cited

U.S. PATENT DOCUMENTS

| | | | |
|---|---|---|---|
| 6,406,848 B1 * | 6/2002 | Bridgham | B01J 19/0046 435/288.3 |
| 6,527,890 B1 | 3/2003 | Briscoe et al. | |
| 6,544,734 B1 | 4/2003 | Briscoe et al. | |
| 6,572,830 B1 | 6/2003 | Burdon et al. | |
| 6,605,451 B1 | 8/2003 | Marmaro et al. | |
| 6,610,499 B1 * | 8/2003 | Fulwyler et al. | 435/7.1 |
| 6,875,619 B2 * | 4/2005 | Blackburn | 506/9 |
| 6,984,516 B2 | 1/2006 | Briscoe et al. | |
| 2002/0064482 A1 * | 5/2002 | Tisone et al. | 422/100 |
| 2003/0118481 A1 | 6/2003 | Briscoe et al. | |
| 2003/0129646 A1 | 7/2003 | Briscoe et al. | |
| 2003/0186250 A1 * | 10/2003 | Shah | 435/6 |
| 2005/0042639 A1 | 2/2005 | Knapp et al. | |
| 2005/0064465 A1 | 3/2005 | Dettloff et al. | |
| 2005/0089862 A1 | 4/2005 | Therianos et al. | |
| 2005/0186590 A1 | 8/2005 | Crothers et al. | |
| 2006/0024690 A1 | 2/2006 | Kao et al. | |
| 2006/0073503 A1 * | 4/2006 | Maeda et al. | 435/6 |
| 2006/0078929 A1 * | 4/2006 | Bickel et al. | 435/6 |
| 2006/0177844 A1 | 8/2006 | Ching et al. | |
| 2008/0085521 A1 | 4/2008 | Knapp et al. | |
| 2009/0081655 A1 | 3/2009 | Therianos et al. | |
| 2012/0244534 A1 | 9/2012 | Ching et al. | |

FOREIGN PATENT DOCUMENTS

| | | |
|---|---|---|
| WO | WO-03048377 A2 | 6/2003 |
| WO | WO-2005003395 A1 | 1/2005 |
| WO | WO-2006047777 A2 | 5/2006 |

OTHER PUBLICATIONS

French patent Office Search Report and Written Opinion dated Dec. 7, 2012.

Robin Hui Liu et al., Self-contained, Fully Integrated Biochip for Sample Preparation, Polymerase Chain Reaction Amplification, and DNA Microarray Detection, Analytical Chemistry, American Chemical Society, vol. 76, Nr. 7, pp. 1824-1831 (Apr. 2004).

Robert M. Umek et al., Electronic Detection of Nucleic Acids, Journal of Molecular Diagnostics, American Society for Investigative Pathology, vol. 3, No. 2, pp. 74-84 (May 2001).

Yi Sun et al., Polymeric Microfluidic System for DNA Analysis, Analytica Chimica Acta, pp. 80-96 (Jan. 2006).

GB Examination Report dated Jun. 22, 2010 in corresponding GB Application No. GB0711618.9.

Discrimination of *Listeria* monocytogenes from other *Listeria* Spicies by Ligase Chain Reaction, Weidmann et al., PCR Methods Appl. Aug. 1991;1(1):5-16.

Liao, C.S. et al. Miniature RT-PCR system for diagnosis of RNA-based viruses. Nucleic Acids Res. (2005) 33 (18) e156, p. 1-7.

Great Britain Search Report dated Oct. 17, 2007.

* cited by examiner

ARRANGEMENT FOR DETERMINING THE CONCENTRATION OF NUCLEIC ACIDS

PRIORITY STATEMENT

This application is a divisional application of U.S. Ser. No. 11/808,835, filed on Jun. 13, 2007, which claims priority under 35 U.S.C. §119 from German patent application number DE 10 2006 027 675.2 filed Jun. 14, 2006, the entire contents of each of which is incorporated herein by reference.

FIELD

Embodiments of the invention generally relate to a process for determining the concentration of nucleic acids in a sample in a microfluidic device and/or to an arrangement for carrying out the process. It is noted here that the term "nucleic acid" is intended to include nucleic acid sequences in the context of embodiments of the present invention. Examples of these may be DNA or RNA sequences.

BACKGROUND

Many problems in molecular-biological research and diagnostics require determining the amount or concentration of particular nucleic acids in a sample. For example, controlling the course of therapy in AIDS patients requires determining the number of copies of viral nucleic acids of the HIV virus (the "viral load") in the blood. Since the nucleic acid to be determined is frequently present in a mixture with many other nucleic acids and, in addition, has a very low initial concentration, it is usually necessary to amplify and specifically detect the nucleic acid (or nucleic acids) to be determined.

There are various processes known in molecular biology for specific amplification (propagation) of nucleic acids, for example the polymerase chain reaction (PCR) which is described inter alia in U.S. Pat. No. 4,683,195. In addition, the PCR method is also suitable for quantifying nucleic acids, for example by including a known nucleic acid having a known initial concentration (of an internal standard) in the PCR reaction, wherefrom the initial concentration of other nucleic acids being detected in the sample can be inferred, as described in U.S. Pat. No. 5,219,727. Since in this case the concentration is determined only after the PCR reaction has been completed, this is referred to as an "end point method".

In addition, methods have been developed which enable concentrations to be determined in the course of the PCR reaction and which are referred to as real time methods (real time PCR). Since, under ideal conditions, the number of the nucleic acids to be amplified can be doubled in each reaction cycle of the PCR, amplification is exponential. In real time PCR processes, the increase in concentration of the amplified nucleic acids can be monitored in real time, for example by incorporation of a fluorescent dye.

Further optical, mass-spectrometric and electrochemical processes for determining concentrations are also known.

Another process for amplifying nucleic acids is the ligase chain reaction (LCR) which is carried out similarly to a PCR but in which the enzyme used is a nucleic acid ligase, see, for example, Wiedmann et al. "Discrimination of Listeria monocytogenes from other Listeria species by ligase chain reaction", Appl Environ Microbiol. 1992, November; 58(11):3443-7.

Disadvantageously, however, these methods have a limited dynamic range. The typical dynamic range is between 1 to 100 and 1 to 1,000, but the range of nucleic acid concentrations to be measured often is distinctly larger, for example 1 to 1,000,000. The determination of concentrations therefore frequently requires serial dilutions to be made, for example 1 in 1, 1 in 10, 1 in 100, etc., in order to enable the concentration to be measured subsequently within the measurement range of the determination method. This is time-consuming and requires additional resources and is an additional source of error. A particular problem here is the sigmoidal time course profile of the concentration of the PCR product being produced, which is caused inter alia by the PCR reagents (primer, nucleoside triphosphates, etc.) being gradually used up with advanced reaction time (large number of PCR cycles), and/or the saturation zone of the detection method being reached. At this time, the concentration can no longer be determined in any meaningful sense.

SUMMARY

In at least one embodiment, the present invention generates a process which limits or even removes at least one of the abovementioned disadvantages.

According to at least one embodiment of the invention, a process is disclosed. According to at least one other embodiment a corresponding arrangement for carrying out the process is disclosed.

According to at least one embodiment of the present invention, a process for determining the concentration of nucleic acids in a sample in a microfluidic device is provided, which has the following steps:

a) introducing the sample into a first chamber,
b) carrying out a predetermined number of cycles of an amplification reaction to be carried out in cycles for amplifying nucleic acids,
c) transferring a defined volume which is a fraction of the volume of the first chamber and which has amplified nucleic acids into a second chamber and replacing the transferred part of the sample volume with fresh reagents for the amplification reaction,
d) determining the concentration of the amplified nucleic acids in a second chamber equipped with means of determining concentrations, and
e) repeating steps b)-d) until a concentration of the amplified nucleic acids which is within a predefined range is determined in the second chamber,
wherein said predefined range is the measurement range of said means of determining said concentration.

It is emphasized here that the predetermined number of cycles of the amplification reaction according to one aspect of the invention can vary from one repeated step to the next. Thus, for example, it is conceivable to run 20 cycles in a first round and 10 cycles in a second round and 5 cycles in a third round.

A "reaction to be carried out in cycles for amplifying nucleic acids" means in the context of the present invention a reaction in which the nucleic acids are propagated step-by-step in individual reaction steps, for example they are doubled in each case. It is possible, by altering the cycles of particular reaction parameters (e.g. temperature) to optionally stop or continue reactions of this kind after a predetermined number of steps (i.e. cycles). Preference is given to using the polymerase chain reaction (PCR) as reaction to be carried out in cycles for amplifying nucleic acids. However, the process of the invention can also be carried out with any other amplification reaction which can be carried out in cycles, for example LCR.

Transferring the defined volume to the second chamber and replacing the transferred volume with fresh reagents for the reaction to be carried out in cycles may take place as a single step, for example by displacing the volume from the first chamber into the second chamber by a corresponding volume of fresh reaction solution. It is however also conceivable to carry out the transfer and the replacement in separate steps.

The term microfluidic denotes processes in which fluid volumes in the μl range are manipulated. The microfluidic device may be designed with channels and cavities in which the process can be carried out. Preference is given to the microfluidic device being designed as a card-like flat construct, a "cartridge", in which the channels and cavities are designed for controlling the reaction. The reagents for the cyclic amplification reaction may comprise reaction buffers (e.g. in the form of the corresponding salts), enzyme, nucleoside triphosphates and primers (oligonucleotides). The reagents may be provided in a storage-stable form, for example dried, or under a paraffin layer which can be removed by melting, already in the microfluidic device.

The predetermined concentration range is the measurement range of the means of determining the concentration.

The concentration of the amplified nucleic acids may be determined unspecifically, for example by an optical process (e.g. by absorption spectrometry or fluorescence, for example by incorporating a fluorescent dye in amplified nucleic acids).

According to another aspect of the present invention, preference is however given to detecting the amplified nucleic acids sequence-specifically, with the means of determining the concentration of the nucleic acids having a microarray in which capture oligonucleotides for binding the amplified nucleic acids have been immobilized (spotted) position-specifically on a support.

The concentration of the amplified nucleic acids bound is preferably determined utilizing a label. This label may be, for example, an optical label or an enzymatic label. The enzymatic label may catalyze an enzymatic reaction which can be detected optically, or can preferably catalyze an enzymatic reaction which can be detected electrochemically. Electrochemical detection offers many advantages, for example simple signal processing of the signals being produced and the less complex construction of the evaluation apparatus in comparison with optical methods. According to a further aspect of the invention, preference is given to the electrochemical reaction being a measurement of currents, enhanced by means of redox cycling.

The original concentration of the nucleic acid or nucleic acids to be determined may be determined, for example, by using an internal standard (a known nucleic acid with a known initial concentration, which is added to the sample or is amplified and measured in parallel) whose concentration after amplification can be used for inferring the original concentration of nucleic acids in the sample. Furthermore, it is also possible to calculate the nucleic acids in the sample on the basis of the volume ratio of the transferred defined volume to the total sample volume and on the basis of the number of PCR cycles carried out.

At least one embodiment of the invention further relates to an arrangement for carrying out the process of at least one embodiment of the invention, which arrangement has a microfluidic device with a first chamber with heating/cooling device/element for amplifying nucleic acids by way of an amplification reaction to be carried out in cycles and having a second chamber which can be connected to the first chamber by way of fluidic communication and which is equipped with an element for/way of determining concentrations of amplified nucleic acids, wherein the arrangement comprises a device/element for introducing a defined volume of a solution containing reagents for the amplification reaction into the first chamber and of transferring a defined volume from the first chamber to the second chamber, wherein a control unit of the device/element for introducing a defined volume of a solution into the first chamber and of transferring a defined volume from the first chamber to the second chamber are provided for.

The control unit is preferably designed in such a way that it can receive a signal from the means of determining concentrations and, as a response to said signal, controls the means of introducing the defined volume of the solution containing amplification reagents into the first chamber and of transferring said defined volume from the first chamber to the second chamber, in order to supply said first chamber with fresh solution containing amplification reagents. Further preference is given to the control unit being able to control the amplification reaction cycles, for example by predefining a temperature profile for means of heating and/or cooling the first chamber. If, in a first concentration measurement after a first round of amplification reaction cycles, for example, the control unit receives a signal that the concentration is still below a predetermined range, said control unit can effect another round of cycles by controlling a temperature profile in the first chamber.

The entire analytical procedure can be accelerated by starting or implementing the other cycles even while the steps of determining concentrations, such as hybridization, coupling of the label and detection of the already amplified nucleic acids, are carried out with the transferred volume portion.

According to another aspect of the present invention, the arrangement also has preferably a computer which is designed for calculating the concentration of a nucleic acid in a sample on the basis of a signal of the means of determining concentrations. Said computer may be microprocessor-controlled, and the hardware and software requirements for operating such a computer are known to the skilled worker.

According to another aspect of the present invention, the arrangement further has preferably at least one reservoir containing reagents which are used for detecting nucleic acids. Said reservoir may contain, for example, an enzyme label (i.e. an enzyme which can be used for labeling nucleic acids) or an enzyme substrate which is converted by enzyme-labeled nucleic acids. Preference is given to designing the microfluidic device with said reservoir.

BRIEF DESCRIPTION OF THE DRAWINGS

Further features and advantages of the present invention arise from the following description of the figures of example embodiments and on the basis of the appended drawings which are by way of example and illustration only and in which.

DETAILED DESCRIPTION OF THE EXAMPLE EMBODIMENTS

Figure 1:
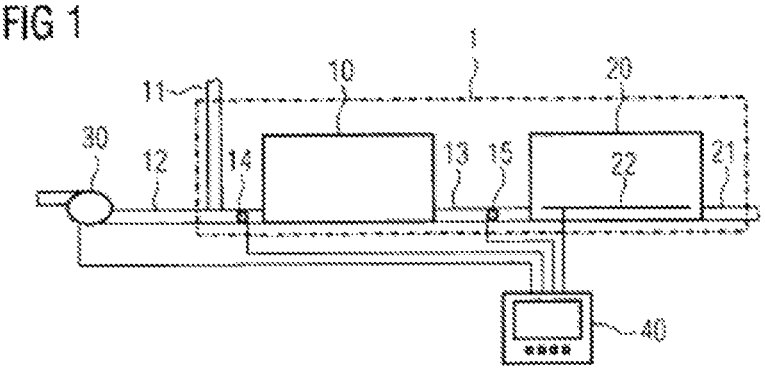
FIG. 1 depicts a diagrammatic representation of an arrangement for carrying out the process of an embodiment of the invention.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, terms such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described. Like numbers refer to like elements throughout. As used herein, the terms "and/or" and "at least one of" include any and all combinations of one or more of the associated listed items.

FIG. 1 depicts an arrangement for performing the process of the invention, with a microfluidic cartridge 1 (represented by the dashed line), having a first chamber 10 and a second chamber 20. A sample containing nucleic acids to be studied can be introduced via a supply line 11 and a first line 12 into the chamber 10. An element/device for heating and/or cooling (not shown) are designed at chamber 10. On the side of the cartridge, this may be a region with a particularly high heat conductivity, for example due to appropriately thin material walls, it being possible for heating and cooling elements, for example Peltier elements, to be assigned to the cartridge. Upon introduction of the sample, the chamber may already contain reagents for carrying out a PCR reaction (reaction buffer, enzyme, nucleoside triphosphates, primers, etc.), for example in dry form, so that they are dissolved when the liquid sample is introduced, or they may also be mixed, for example, with the sample and introduced through the supply line 11 and the first line 12.

A second line 13 to the second chamber 20 is also designed. The lines 12, 13 may be closed selectively via a first valve 14 and a second valve 15, respectively. The valves 14, 15 are opened, after a PCR reaction with a predetermined number of cycles (for example 20 cycles) has been carried out. A defined volume, which is a fraction of the volume of the first chamber, of a solution with fresh PCR reagents (e.g. reaction buffer, enzyme, nucleoside triphosphates, primers, etc.) can then be supplied via a means 30 and via the line 12 into the chamber 10. The volume transfer means 30 may be a controllable metering pump, a reciprocating pump or a similar means which can be used to move a defined volume. As a result, a corresponding portion of the volume of the chamber 10 is displaced and transferred to the chamber 20.

An element 22 for/way of determining the concentration of the nucleic acids is designed in the chamber 20. Excess volume can be displaced from the chamber 20 via a drain 21. The concentration of amplified nucleic acids in the transferred defined volume is determined via the means 22 of determining concentrations and a corresponding signal is transmitted to the control unit 40. If the concentration of the amplified nucleic acids is below the measurement range of the means of determining concentrations, the valves 14 and 15 are closed via the control unit 40 and another round of PCR reaction cycles (e.g. another 10 cycles) is started. After completion of the second round of PCR reaction cycles, the valves 14 and 15 are opened again by the control unit 40 and fresh solution containing fresh PCR reagents is passed via the means 30 and the line 12 into the chamber 10. As a result, a corresponding defined volume containing amplified nucleic acids is again transferred into the chamber 20.

There, the concentration is determined via the means of determining concentrations 22, and this process is repeated until the concentration of the amplified nucleic acids is within the measurement range. Then a final concentration determination can be carried out, and the initial concentration of the nucleic acids to be determined can be inferred from the known reaction kinetics of the PCR reaction, the number of cycles and the proportion of the transferred volumes of the total sample volume. This may be carried out by a connected computer which can calculate the concentration on the basis of the measured signals and the other information about the number of reaction cycles, sample volumes etc.

Figure 2:
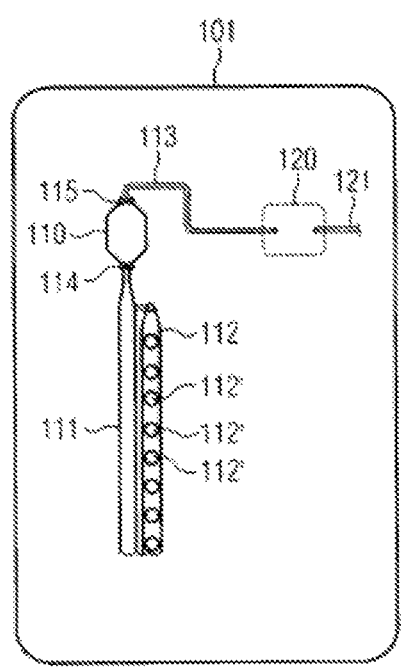
FIG. 2 depicts a diagrammatic partial representation of a microfluidic device in the form of a cartridge which can be used in an arrangement for carrying out the process of an embodiment of the invention.

According to an embodiment of the invention, the chambers 10 and 20, and also the supply, connecting and discharge lines 11, 12, 13 and 21 are designed in a microfluidic device 1. Referring to FIG. 2, the last two digits of the reference numbers of analogous elements, such as in FIG. 1, correspond to the respective reference number in FIG. 1, so that the first chamber 10 of FIG. 1 is accordingly indicated in FIG. 2 by the reference number 110, etc.

Referring now to FIG. 2, a cartridge 101 consists of a plastic body incorporating depressions or microchannels and other structures which are described below.

The intended reagents may be spotted as dry reagents into the cartridge 101. The PCR reagents for the first round of reaction cycles may be provided directly in the first chamber (the PCR chamber) 110. A microarray in the form of a chip is designed as a means of determining the concentration in the chamber 120. PCR reagents for further rounds of PCR cycles may be provided as dry reagents in the depressions 112' in the first line 112. After spotting the reagents on the top side, the cartridge may be sealed by a film, for example.

The sample may be introduced through the channel 111 into the first chamber (PCR chamber) 110. The first chamber may be closed with a first valve 114 and a second valve 115. To carry out the process, the cartridge is then introduced into an apparatus which includes the control unit, heating elements, possible means of supplying water or buffer and the like (not shown). The PCR chamber 110 may be heated and/or cooled by heating and/or cooling elements (e.g. Peltier elements), so that the PCR reaction cycles can be carried out via a control unit (not shown) on the basis of a predefined temperature profile, as known to the skilled worker.

After a predefined number of cycles, the valves 114, 115 are opened, and, via the first line 112, a defined volume of a solution is introduced by a volume transfer means located outside the cartridge (not shown) into the cartridge and, as a result, displaces a corresponding volume of the sample containing amplified nucleic acids from the chamber 110. The solution may already contain fresh PCR reagents.

Alternatively, fresh PCR reagents, for example in dried form, may also be present in the first line 112 in the depressions 112' so that, when a solvent (e.g. water or buffer) is pumped through the first line 112, the dry PCR reagents are dissolved and then introduced in solution into the chamber 110. The corresponding, displaced part of the sample volume is transferred via the second line 113 into the chamber 120, where the concentration is determined. In this way, the solution containing fresh PCR reagents is introduced and a defined volume is transferred in a single step, with fresh PCR reagents already being available in the first chamber for a possible further round of PCR cycles. The amplified nucleic acids may be labeled, for example by using biotinylated primers, in order to make subsequent detection possible.

The displaced volume reaches the chamber 120. There, a microarray is located in the form of a microarrangement (spotted onto a support) of capture oligonucleotides with known sequences, which can bind the amplified nucleic acids, which microarrangement is immobilized on a support. Detection is carried out electrochemically as described, for example, in the laid-open specification DE 101 26 341 A1, the entire contents of which are hereby incorporated herein by reference.

For this purpose, two electrodes per detection spot are located on a silicon surface, which, as an electrode arrangement of anode and cathode, form an interdigital structure containing interlocking electrode fingers via which a current can be picked up. For detection, an enzyme is introduced into the detection chamber, for example streptavidin-conjugated alkaline phosphatase. The latter binds to the biotin-labeled amplified nucleic acids. Subsequently, an enzyme substrate is introduced into the detection chamber 120.

An example of a substrate which may be supplied is p-aminophenyl phosphate which is converted to para-aminophenol by the alkaline phosphatase bound to the amplified nucleic acids. p-Aminophenol is oxidized on the electrode system, or the redox pair p-aminophenol/quinonimine is cyclized, as described in DE 101 26 341 A1. This results in a measurable increase in current at the electrodes. The signal picked up in this way may be processed on a connected computer.

If a first round of PCR reaction cycles has not produced enough amplified nucleic acids, the signal will be below the measurement range. In this case, the control unit enables a new round of PCR cycles to be carried out. This may be continued until the amplified nucleic acids have reached a concentration which is within a desired range, for example within the measurement range of the means of determining a concentration.

For example, 10 cycles may be run in a first PCR reaction cycle. Subsequently, for example, half the volume of the first chamber is transferred and a first concentration determination is carried out. The other half of the volume which remains in the PCR chamber is admixed with the corresponding volume of fresh PCR reaction buffer, and it is then possible to run another 10 cycles in a second round in order to determine the concentration again. If the dynamic measurement range of the concentration determination means (e.g. 1:1000) is known, the number of cycles in the particular PCR reaction rounds may be appropriately chosen so as to achieve a continuous coverage of a continuous concentration range.

It is emphasized here that the example embodiment is described by way of example only and that many variations with regard to the arrangement of chambers and lines (channels), to the type of detection and reaction control, are conceivable. The important point here is that, by interrupting the amplification reaction and transferring part of the sample volume and replacing the transferred volume portion with fresh amplification reaction buffer in a simple and integrated process, a concentration can be determined over a substantially greater range than the measurement range of the element for/way of determining said concentration.

Further, elements and/or features of different example embodiments may be combined with each other and/or substituted for each other within the scope of this disclosure and appended claims.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An arrangement, comprising:
a microfluidic device including,
a first chamber with an element for amplifying nucleic acids by means of an amplification reaction to be carried out in cycles,
a second chamber, connectable to the first chamber by way of fluidic communication, equipped with an element to determine concentrations of amplified nucleic acids, and
at least one valve for interrupting and/or releasing fluidic communication between the chambers;
a single pump to transfer nucleic acids; and
a control unit to control the at least one valve and the pump, and to introduce a defined volume of a solution containing reagents for the amplification reaction into the first chamber and to transfer a defined volume from said first chamber to the second chamber, wherein said control unit is connected to the second chamber, said pump and said at least one valve and being responsive to a signal transmitted from said element of the second chamber to said control unit for operating said pump and/or said at least one valve based on the concentration of amplified nucleic acids determined by said element.

2. The arrangement as claimed in claim 1, wherein the element of the second chamber to determine the concentration includes a microarray having position-specifically immobilized capture oligonucleotides for detecting the amplified nucleic acids.

3. The arrangement as claimed in claim 1, further comprising at least one electrochemical detection element configured for measuring at least one of currents and potentials.

4. The arrangement as claimed in claim 1, further comprising one of a heating and a cooling device configured for amplifying nucleic acids by way of an amplification reaction to be carried out in cycles.

5. The arrangement as claimed in claim 4, wherein the control unit is further designed for providing a temperature profile for the at least one of a heating and cooling device for the first chamber.

6. The arrangement as claimed in claim 1, further comprising a computer to calculate the concentration of a nucleic acid in a sample on the basis of a signal of the element of the second chamber to determine the concentration.

7. The arrangement as claimed in claim 1, further comprising at least one reservoir of reagents for determining the concentration of nucleic acids, the reservoir being connectable to the second chamber by way of fluidic communication.

8. The arrangement as claimed in claim 7, wherein the reservoir comprises an enzyme label.

9. The arrangement as claimed in claim 7, wherein the reservoir comprises an enzyme substrate.

10. An arrangement, comprising:
   a microfluidic device in form of a cartridge including,
   a first chamber with an element for amplifying nucleic acids of a sample by means of an amplification reaction to be carried out in cycles,
   a second chamber, connectable to the first chamber by way of fluidic communication, equipped with an element to determine concentrations of amplified nucleic acids, the concentration of the amplified nucleic acids are determined using an enzymatic label,
   wherein the element of the second chamber is configured for determining the concentrations of the amplified nucleic acids based on an electrochemical signal generated by an enzymatic reaction catalyzed by the enzymatic label,
   a channel through which the sample is introduced into the first chamber, and
   at least one valve for interrupting and/or releasing fluidic communication between the chambers,
   wherein the first chamber contains reagents in dry form carrying out the amplification reaction;
   a single pump to transfer nucleic acids; and
   a control unit to control the valve and the pump, and to introduce a defined volume of a solution containing reagents for the amplification reaction into the first chamber and to transfer a defined volume from said first chamber to the second chamber,
   wherein the arrangement is configured to transfer defined volumes of amplified nucleic acids subsequently to the second chamber based on the electrochemical signal.

* * * * *